US011372176B2

(12) United States Patent
Van Schuylenbergh et al.

(10) Patent No.: US 11,372,176 B2
(45) Date of Patent: Jun. 28, 2022

(54) IMPLANTABLE OPTICAL SENSOR WITH HERMETICALLY SEALED COVER CAP

(71) Applicant: Indigo Diabetes N.V., Zwijnaarde (BE)

(72) Inventors: Koenraad Van Schuylenbergh, Vorselaar (BE); Danaë Delbeke, Gentbrugge (BE); Paolo Cardile, Ghent (BE)

(73) Assignee: Indigo Diabetes N.V., Zwijnaarde (BE)

( * ) Notice: Subject to any disclaimer, the term of this patent is extended or adjusted under 35 U.S.C. 154(b) by 273 days.

(21) Appl. No.: 16/500,097

(22) PCT Filed: Mar. 30, 2018

(86) PCT No.: PCT/EP2018/058325
§ 371 (c)(1),
(2) Date: Oct. 2, 2019

(87) PCT Pub. No.: WO2018/185032
PCT Pub. Date: Oct. 11, 2018

(65) Prior Publication Data
US 2020/0310051 A1    Oct. 1, 2020

(30) Foreign Application Priority Data

Apr. 3, 2017    (EP) .................................... 17164567

(51) Int. Cl.
*A61B 5/1455*        (2006.01)
*G02B 6/42*          (2006.01)
(Continued)

(52) U.S. Cl.
CPC .......... *G02B 6/4251* (2013.01); *A61B 5/0031* (2013.01); *A61B 5/1459* (2013.01); *A61B 5/14532* (2013.01); *G02B 6/4245* (2013.01); *G02B 6/4257* (2013.01); *G02B 6/4277* (2013.01); *A61B 2562/0233* (2013.01);
(Continued)

(58) Field of Classification Search
None
See application file for complete search history.

(56) References Cited

U.S. PATENT DOCUMENTS 6,981,806 B2    1/2006  Benzoni et al.
2004/0176669 A1    9/2004  Colvin, Jr.
(Continued)

FOREIGN PATENT DOCUMENTS

| EP | 0845690 A2 | 6/1998 |
| EP | 0845690 A3 | 6/1998 |
| WO | 2016137444 A1 | 9/2016 |

*Primary Examiner* — Marjan Fardanesh
(74) *Attorney, Agent, or Firm* — N.V. Nederlandsch Octrooibureau

(57) ABSTRACT

An implantable optical sensor comprises a photonic integrated circuit comprising a substrate 2 and an optical microstructure 3 integrated with the substrate 2. The optical microstructure is positioned to form an exposed optical interaction area 4 on a part of a surface 5 of the substrate 2. A cover cap 6 is sealed onto a part of the substrate 2 adjacent to the optical interaction area 4 and by wafer-to-wafer bonding technology or another wafer-level hermetic packaging technique. At least one active component 8 is positioned in a sealed cavity 9 which is formed between the surface 5 and the cover cap 6. The substrate 2 comprises at least one optical feedthrough 10, which is an embedded waveguide extending from the sealed cavity 9 to the optical interaction area 4.

18 Claims, 3 Drawing Sheets

(51) Int. Cl.
  *A61B 5/00*    (2006.01)
  *A61B 5/145*   (2006.01)
  *A61B 5/1459*  (2006.01)
(52) U.S. Cl.
  CPC ..... *A61B 2562/12* (2013.01); *A61B 2562/182* (2013.01); *A61B 2562/227* (2013.01); *A61B 2562/228* (2013.01)

(56) References Cited

U.S. PATENT DOCUMENTS

| | | |
|---|---|---|
| 2004/0245425 A1 | 12/2004 | Delpiano et al. |
| 2005/139644 A1 | 6/2005 | Brese et al. |
| 2005/285131 A1 | 12/2005 | Gallup et al. |
| 2009/154872 A1 | 6/2009 | Sherrer et al. |
| 2017/0017050 A1 | 1/2017 | Gamache et al. |
| 2017/0071510 A1 | 3/2017 | Delbeke et al. |

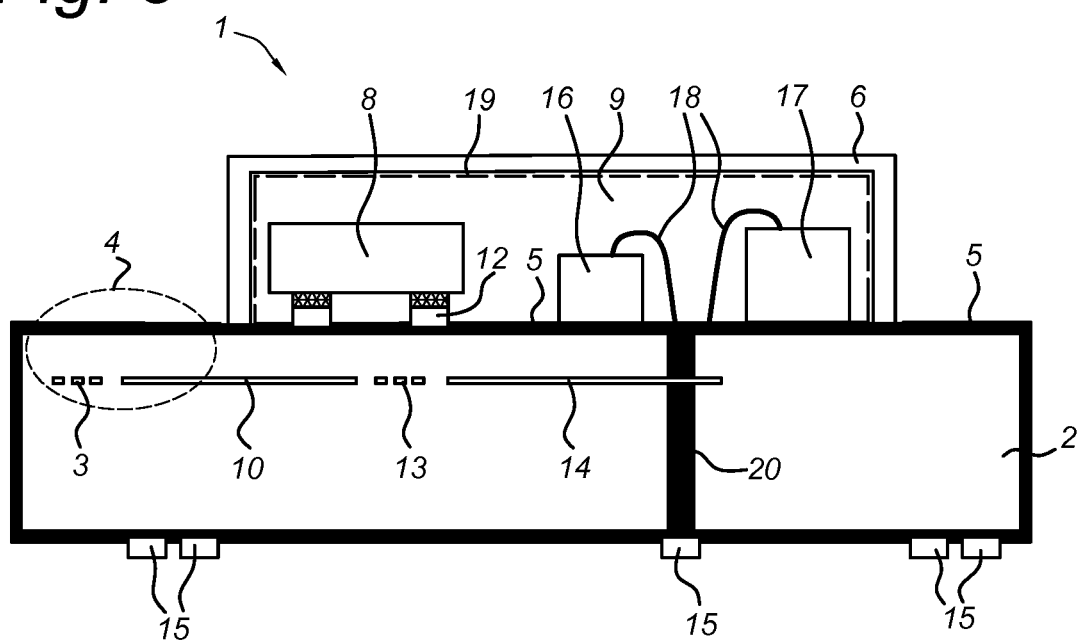
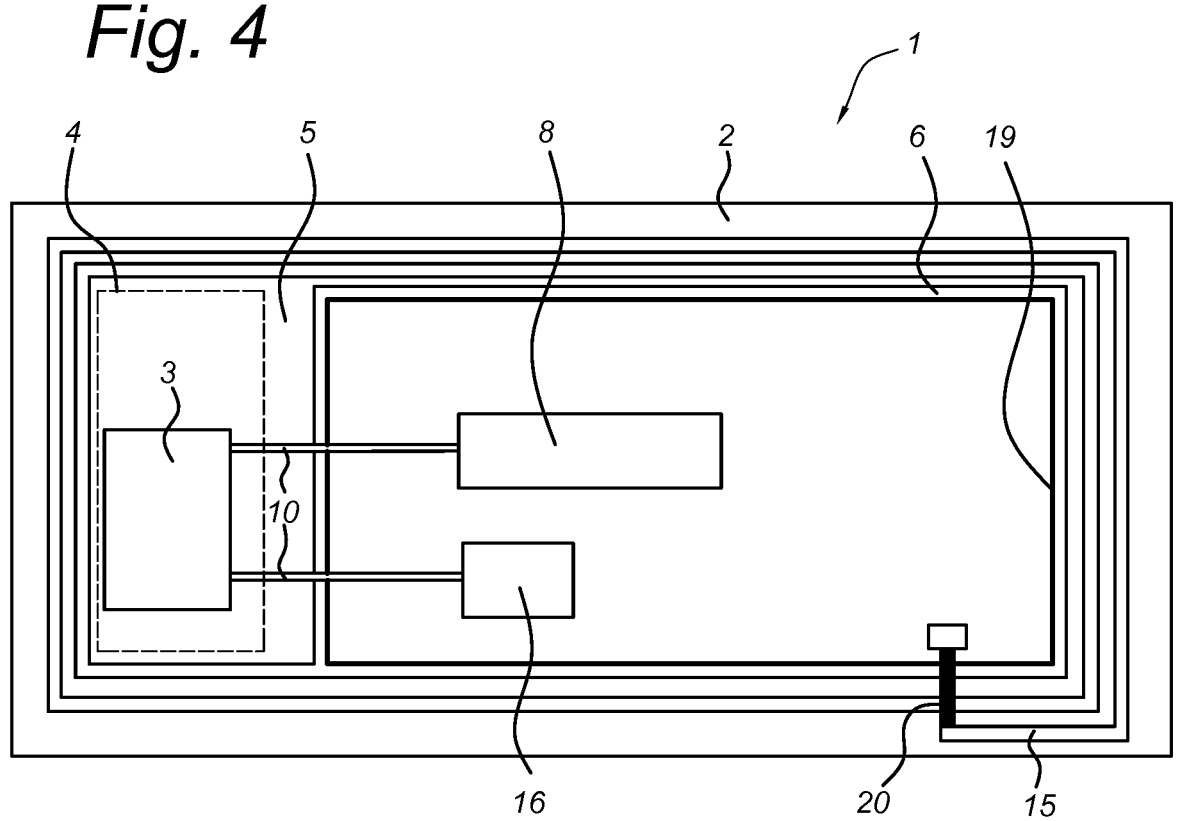

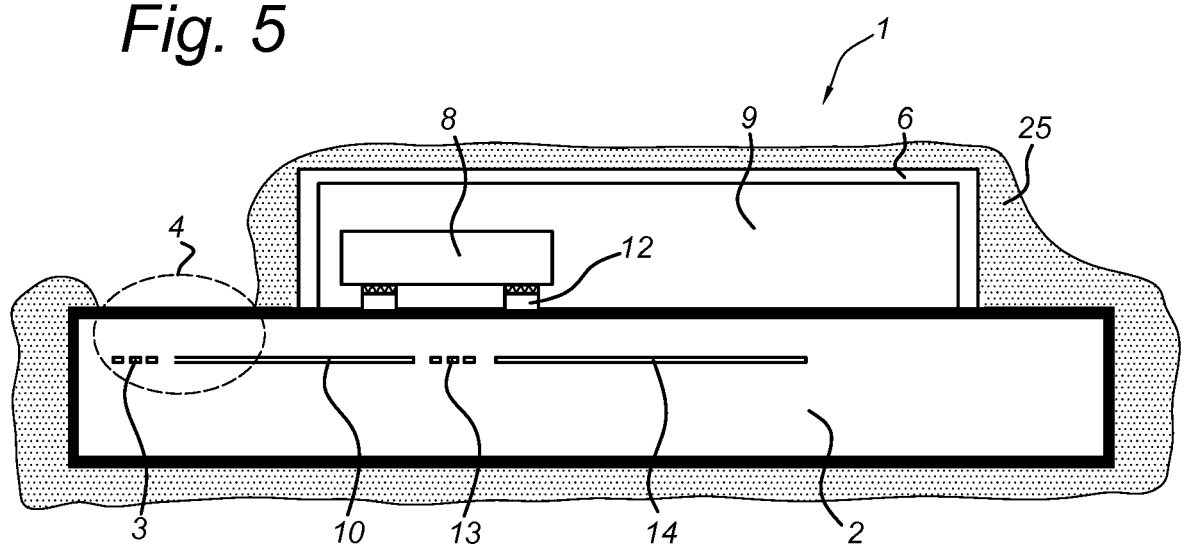

IMPLANTABLE OPTICAL SENSOR WITH HERMETICALLY SEALED COVER CAP

FIELD OF THE INVENTION

The present invention relates to an optical assembly, e.g. an implantable optical sensor, comprising a substrate and an optical microstructure integrated with the substrate, the optical microstructure being positioned to form an optical interaction area on a part of a surface of the substrate. In a further aspect, the present invention relates to a method of manufacturing an optical assembly, the method comprising providing a substrate with an integrated optical microstructure forming an optical interaction area.

BACKGROUND ART

International Patent publication WO2016/137444 discloses a sensor and a method for measuring an analyte in a medium within a living animal. The sensor includes an inductive element, a charge storage device and a memory. The sensor performs analyte measurements initiated by an external device using power received from the external device and conveys analyte measurements to the external device using the inductive element. The sensor is entirely sealed in a glass capsule US patent publication U.S. Pat. No. 6,981,806 B2 discloses a method for micro-hermetic packaging an optical device. The method comprises forming a micro-hermetic cavity on a substrate, providing a transmission optical waveguide on the substrate and sealing an optical device within the micro-hermetic cavity. A lid separate from the first substrate is employed for the sealing process or the micro-hermetic cavity is provided on the lid and sealed on to the first surface. The optical device may be positioned within the cavity for optical power transfer with the optical waveguide.

US 2004/0245425 A1 discloses a hybrid electro-optical device which has a portion defining a mounting location for optoelectronic components such as laser sources, photodetector diodes, LEDs, requiring local hermetic protection of the bare chips. A planar lightwave circuit (PLC) waveguide structure formed on the substrate extends to the mounting location to define an optical signal feed-through for the device. At least one electrode is associated with the planar lightwave circuit waveguide structure and extends said mounting location to define an electrical signal feed-through for the device. A ring-like structure continuously surrounds said mounting location and a continuous cover member is soldered thereon to cover and hermetically seal the mounting location. As a result of this ring-like structure, which is a metal rim, the device is not suitable for wafer scale production.

A well-known approach in art used to protect optical assemblies is by using e.g. a titanium box. However this approach has the drawbacks of not being a wafer scale process and each device needs to be processed separately, thereby making the approach costly. If an optical measurement needs to be carried out in an optical assembly, a feedthrough needs to be foreseen; which is not standard. A further approach is using parylene-c coating, but then it is not possible to test a device for a successful hermetic packaging. Another approach used, e.g. in telecommunications, and data communications applications, is by using a wafer scale capping in which the feedthroughs are made through the wafer scale cap. These feedthroughs are weak points especially when regarded in relation to a desired long life time.

SUMMARY OF THE INVENTION

The present invention seeks to provide an optical assembly, e.g. an implantable optical sensor, which is particularly suited to interact optically with harsh environments. More in particular, the present invention seeks to provide an optical assembly having an optical interaction area to provide exposure to a fluid, such as body fluids, as well as associated further active components which are sealed from the fluid, in order to have a reliable and safely working optical assembly. Further, the present invention seeks to provide an optical assembly which can be produced by wafer scale processes.

According to the present invention, an optical assembly as defined above is provided, further comprising a cover cap on a part of the substrate adjacent to the optical interaction area. At least one active component is positioned in a sealed cavity which is formed between the surface and the cover cap. The substrate comprises at least one optical feedthrough extending from the sealed cavity to the optical interaction area. As a result, there is no need to protrude the cover cap for reasons of communicating or interfacing with electronic components within the sealed cavity. This effectively shields the electronic component, and more specifically the electrical components of the optical assembly from contact with the fluid during use, without influencing the optical properties and measurement capabilities of the optical assembly. Furthermore, optical communication is possible from the active component(s) in the sealed cavity to an optical microstructure (which is present on the substrate) and back.

The cover cap is hermetically sealed to said substrate part by wafer-to-wafer bonding technology or another wafer-level hermetic packaging technique. The resulting device may be characterized by absence of any metal rim or ring-like structure as described in US 2004/0245425 A1 to prepare the substrate for sealing the cover cap thereto, absence of soldering material between the cover cap and the substrate, i.e. the bottom edge of the cap may be in direct contact with the surface of the substrate. Furthermore, the resulting device may be characterized by absence of a flange at the bottom edge of the cover cap, i.e. the techniques used for sealing the cap onto the substrate do not require such a flange.

A further aspect the present invention relates to a method of manufacturing an optical assembly as defined above, wherein the method further comprises providing at least one active component on the surface adjacent to the optical interaction area, and providing a cover cap on a part of the substrate to form a sealed cavity where the at least one active component is positioned. Furthermore, the method comprises sealing the cover cap to the substrate by wafer-to-wafer bonding technology or another wafer-level hermetic packaging technique, and providing at least one optical feedthrough extending from the sealed cavity to the optical interaction area (i.e. without protruding the cap). As the method uses techniques which are compatible with the manufacturing steps for other elements of the optical assembly, the method can be implemented as an efficient and cost-effective manufacturing method.

SHORT DESCRIPTION OF DRAWINGS

The present invention will be discussed in more detail below, with reference to the attached drawings, in which, FIG. 1 shows a schematic cross sectional view of an optical assembly according to a first embodiment of the present invention;

FIG. 3 shows a schematic cross sectional view of an optical assembly according to a further embodiment of the present invention;

FIG. 4 shows a schematic top view of an optical assembly according to an even further embodiment of the present invention; and FIG. 5 shows a schematic cross sectional view of an optical assembly according to an even further embodiment of the present invention.

DESCRIPTION OF EMBODIMENTS

Optical assemblies which have an intended use as implantable (or (partially) immersed) optical sensors mostly have bulky components in the form of electronic and/or optoelectronic components. These may comprise electronic circuitry requiring an electrical power supply for its operation, and this circuitry must be completely sealed and protected from any moisture. When circuitry is exposed to an environment of the optical assembly during operation, the functioning thereof can be severely affected by the presence of water in liquid or in vapour form. Metallic wire-bonds may fail, metal lines may be corroded and damaged, and the interaction with fluids will just stop the functionality of components. Some of the applications of the optical assembly according to the present invention embodiments include, but are not limited, to sensing body fluids such as blood or interstitial fluid and fluids in chemical processes such as a fermentation tank or a petrochemical tank. Such optical assemblies often have a direct and/or long term interaction of a sensing surface with a hostile environment (e.g. a corrosive environment). Long term interaction or even a short term interaction of a hostile environment can substantially degrade the performance and functioning of electronic and optoelectronic components in the optical assembly. Hence electronic and optoelectronic components which are part of an optical assembly need to be properly packaged to eliminate direct exposure to this undesired environment. The present invention embodiments solve these problems by, in a very general sense, providing an optical assembly, having bulky DC-powered optoelectronic components, with hermetic optical (and if needed electrical) feedthroughs. The main problem is solved by providing an optical assembly which has optical (and electrical) feedthroughs between an optical interaction area exposed to and in direct contact with (corrosive) a fluid and e.g. a read-out IC as implementation of an optoelectronic component that is hermetically sealed. All the electronics and photonics components of the present invention optical assembly embodiments requiring electrical power to be activated are positioned under a hermetic cover cap, in order to achieve a reliable and safely working device.

Figure 1:
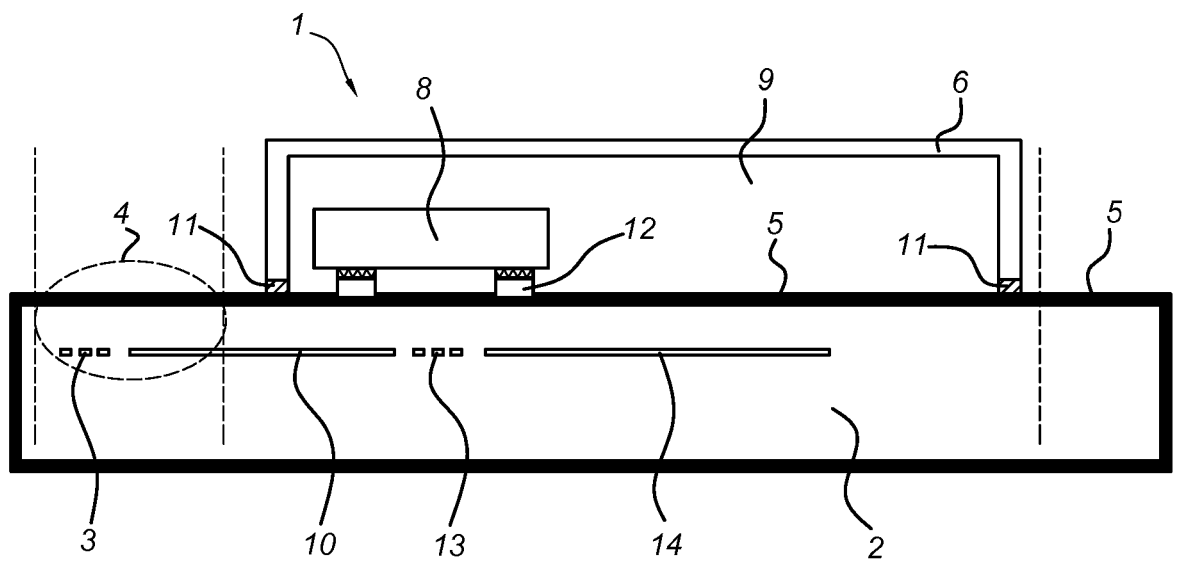

FIG. 1 shows a schematic cross sectional view of a first embodiment of an optical assembly 1 in accordance with the present invention. The optical assembly 1 comprises a substrate 2 and an optical microstructure 3 integrated with the substrate 2. The optical microstructure 3 is positioned (i.e. can be fully or partially embedded, integrated or patterned in the substrate 2) to form an optical interaction area 4. The optical microstructure 3 can comprise one or more of a plurality of integrated optical components such as for example integrated waveguides, gratings, photonic crystals, cavities, micro-ring resonators, couplers, splitters, filters and other optical (tuneable) elements. The optical microstructure 3 can be either active or passive. In the embodiment shown in FIG. 1, the optical microstructure 3 is an embedded waveguide in the substrate 2. As in this embodiment, the optical assembly 1 further comprises a cover cap 6 on a part of the substrate 2 adjacent to the optical interaction area 4 sealed between the cover cap 6 and a surface 5 of the substrate 2. Furthermore, at least one active component 8 is present which is connected to the substrate 2 (e.g. by fixing or bonding the active component to the surface 5 of the substrate 2). The active component 8 is e.g. an electronic component, an optoelectronic component or an optical component, e.g. a signal processor, a photodetector, a light source, a battery, etc. The active component 8 is positioned in a sealed cavity 9 formed between the surface 5 and the cover cap 6. Alternative embodiments use a suitable material for the cover cap 6, which may then be directly heat sealed to the surface 5. The substrate 2 further comprises at least one optical feedthrough 10 extending from the sealed cavity 9 to the optical interaction area 4.

The optical microstructure 3 may be optically connected to the optical feedthrough 10 which is e.g. a waveguide 14 and/or a coupler 13 wherein the coupler 13 is e.g. used for coupling and decoupling of the radiation in and out of the active component 8. One example of a coupler 13 may be an on-chip vertical grating coupler 13 (VGC). The optical assembly 1 according to the embodiment shown in FIG. 1 comprises the optical feedthrough 10, which allows optical communication from inside the hermetically sealed cavity 9 to an exposed optical interaction area 4 and back. The optical feedthrough 10 may be arranged to be optically accessible externally from the optical assembly 1, e.g. from a top surface of the substrate 2 or from a bottom surface of the substrate 2. In one embodiment the optical microstructure 3 can be an integrated waveguide which is connected to the optical feedthrough 10 which is e.g. a further embedded waveguide. In this embodiment, the optical microstructure 3 as an integrated waveguide can be a part of the optical feedthrough 10 which is locally etched open to form the optical interaction area 4.

In a further embodiment, the at least one active component 8 is attached to (a part of) the surface 5 of the substrate 2 which is within the sealed cavity 9, e.g. as shown in this embodiment using an under bump metallisation 12. It will be clear that the at least one active component 8 may be attached to the surface 5 in alternative arrangements, e.g. using other type of hybrid integration techniques.

In the optical microstructure 3, although most of the light is confined within a guiding layer (e.g. implemented as waveguides), a small portion, called the evanescent field, extends out into an external medium (e.g. the substrate 2 material and/or the optical interaction area 4). This evanescent field falls off exponentially as the distance from the waveguide surface increases. The evanescent field is used to interact with the environment for e.g. optical trapping, sensing, exciting. In one of the embodiments of the present invention, the optical microstructures 3 having (surrounding) air as its upper cladding, the extending evanescent field in the optical interaction area 4 is utilised for sensing purposes. In an even further embodiment, the optical interaction area 3 is a sensing area. The optical microstructure 3 may be used as an optical sensor e.g. as an evanescent field optical sensor. In further embodiments, the optical microstructure 3 can alternatively be used for e.g. imaging, Optical Coherence Tomography (OCT) or Laser Doppler Velocimetry (LDV) applications.

In a further embodiment, the optical assembly 1 is a Photonic Integrated Circuit (PIC), which refers to a variety of forms and material systems used for making a photonic circuits. In this embodiment, the optical the optical feed-through 10 may be an embedded waveguide. This includes, for example, low-index contrast waveguide platforms (e.g. polymer waveguides, glass/silica waveguides, $Al_xGa_{1-x}As$ waveguides, $In_xGa_{1-x}AS_yP_{1-y}$ waveguides), high-index contrast waveguides (e.g. Silicon-on-Insulator (SOI), semiconductor membranes), plasmonic waveguides (e.g. with metal layers or metal nano-particles), etc. The optical microstructures 3 can be of materials such as silicon (Si), silicon oxide ($SiO_x$), silicon nitride (SiN, silicon rich or stoichiometric silicon) or from a III-V group or II-VI group materials. In an exemplary embodiment, the present invention relates to an embodiment wherein the optical assembly 1 is a SiN or a SOI material implementation, also referred to as silicon photonics system. Silicon photonics has huge advantage over other material systems for making PICs due to its high index contrast and compatibility with the CMOS fabrication techniques. Due to the CMOS industry, silicon photonics technology has reached a level of maturity that outperforms any other plane chip manufacturing technique by several orders of magnitude in terms of performance, reproducibility and throughput. Silicon photonics ICs can be fabricated with a reproducible and well-controlled wafer scale-processes, meaning that a wafer (typically 200 mm or 300 mm diameter) can contain a high number of photonic integrated circuits. Combined with the commercial availability of large wafers at a relative moderate cost, this means that the price per optical assembly 1 can be very low. The optical microstructure 3 can be a shaped semiconductor waveguide as patterned or embedded in the substrate. In an exemplary embodiment, the optical microstructure 3 is a micro-ring resonator (MRR), which is a compact wavelength selective device. The resonant wavelengths of the MRRs are highly affected by a change in the refractive index of the surrounding medium, which is utilised for using it e.g. as a strong optical sensor for biological and chemical applications. The reference made to the optical microstructure 3 in the present application refers to the structure patterned in its guiding layer (e.g. a patterned device layer (Si) in the case of a SOI optical waveguide).

The optical microstructure 3 can be an integrated optical component, such as an integrated optical cavity, an integrated optical resonator, an integrated optical interferometer, an integrated optical coupler, an optical waveguide, a taper, a tuneable filter, a phase-shifter, a grating, a photonic crystal, a modulator, a detector, a source, a multiplexer, a demultiplexer or a combination thereof, embedded, integrated or patterned in the substrate 2. Fabrication of the optical microstructure 3 can be executed using various techniques, such as using electron beam technology, using a photolithographic process, using a CMOS technology or a combination thereof. This can include semiconductor etching steps and back-end process steps like flip-chipping, bonding, metallisation which are as such known to the person skilled in the art.

Figure 2:
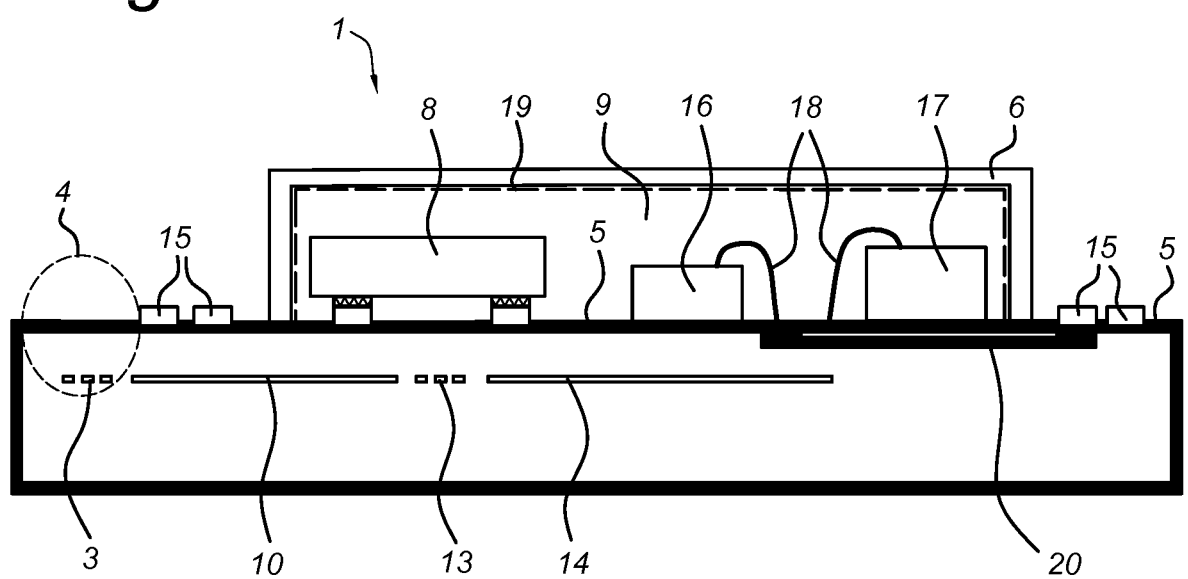
FIG. 2 shows a schematic cross sectional view of an optical assembly according to a second embodiment of the present invention.

In an additional embodiment, the optical assembly 1 further comprises at least one electrical feedthrough 20 extending from the sealed cavity 9 to an area of the substrate 2 outside of the sealed cavity 9. The electrical feedthrough 20 allows electrical power transfer from the electrical or optoelectronic components integrated within the sealed cavity 9 to the external area of the sealed cavity 9. FIG. 2 shows a schematic cross sectional view of an optical assembly 1 according to this additional embodiment of the present invention. In this embodiment, next to the at least one active component 8 (e.g. an optical processing chip), additional electronic or optoelectronic components 16, 17 are connected to the surface 5 within the hermetically sealed cavity 9. The additional electronic devices 16, 17 e.g. comprise power supply unit 16 or an interface circuit 17. The electrical feedthrough 20 is e.g. made with a finishing (or plating) metal which effectively are not affected by being in contact with aggressive fluids. These metal layers will not be deteriorated by any fluids, e.g. a gold, platinum or palladium layer.

In the exemplary embodiment shown in FIG. 2, the electrical feedthrough 20 is connected to an antenna 15, which is positioned outside of the hermetically sealed cavity 9. More general, in a further embodiment, the optical assembly 1 comprises an antenna 15. The antenna 15 in a specific embodiment is connected to the active component 8, e.g. via the electrical feedthrough 20 as shown in the FIG. 2 exemplary embodiment. The antenna 15 can in an alternative further embodiment be placed on the cover cap 6. Inside the sealed cavity 9, the electrical feedthrough 20 is connected to the additional electronic components 16, 17, by means of bonding wires 18 (as such known from electronics packaging techniques). By proper selection and implementation, the antenna 15 can e.g. be used for power and data interfacing to the (opto-)electronic components 8, 16, 17 within the sealed cavity 9. The antenna 15 may be a multi-loop antenna or a different type of antenna, depending on the intended function, operating frequency and modulation type used.

In an alternative or additional embodiment, the electrical feedthrough 20 can extend from the sealed cavity 9 to a surface of the substrate 2 which is opposite to the cover cap 6. Such a via like electrical feedthrough 20 provides an electrical connection from within the sealed cavity 9 to outside, e.g. connection terminals. The electrical feedthrough 20 can be either embedded, patterned or integrated into the surface 5 of the optical sensing assembly 1. An example method to fabricate this electrical feedthrough 20 is by a method called Through-Silicon Via (TSV) of a metal for e.g. copper. TSV is a fabrication method which comprises steps such as etching, deposition of insulator, deposition of barrier and seed layers, and electrochemical plating. Depending on the application, TSV structures differ in size, aspect ratio, density, materials, and technology. TSVs are widely fabricated by means of e.g. deep reactive ion etching (DRIE) which is an extension of the RIE process, a highly anisotropic etch process that is used to generate straight etch profiles, steep trenches or holes in a substrate. TSVs have been demonstrated to be hermetic to fluids, e.g. water.

FIG. 3 shows a schematic cross sectional view of an optical assembly 1 according to an additional embodiment of the present invention. An electrical feedthrough 20 fabricated by the TSV method is used for making electrical connection from the sealed cavity 9 to the antenna 15, which in this embodiment is located on a surface of the substrate 2 opposite of the surface 5 on which the cover cap 6 is attached.

Electro Magnetic Interference (EMI) from the electromagnetic field in the environment can affect the functionality of electronic and optoelectronic components 8, 16, 17 within the sealed cavity 9. This can be avoided by providing an electromagnetic shielding layer 19 as shown in the embodiment of FIG. 2. In a further embodiment of the present invention, the cover cap 6 comprises an electromagnetic shielding layer 19, which acts like a Faraday cage type of shielding. A metal layer is one of the material known in the art as an effective electromagnetic shielding layer, as a full metal sheet or as a mesh layer. The FIG. 2 embodiment shows a cross sectional view of the optical assembly 1 in which the sealed cavity 9 is shielded from outside interference by a protective layer 19 covering completely the inner side of the cover cap 6. Other alternative materials for the protective layer 19 are e.g. conductive polymer composites or conductive polymer nano-composites.

Some applications require that the optical interaction area 4 of the optical assembly 1 is exposed to a fluid environment. The cover cap 6 hermetically shields the electronic and optoelectronic components 8, 16, 17 within the sealed cavity 9 from this fluid environment. Hence the cover cap 6 is made of a fluid-sealing material in a further embodiment. The cover cap 6 is operative in a manner that it will not affect the sensing properties of the exposed optical interaction area 4. This fluid-sealing material can be glass, metal, silicon, polymer, etc. The metal can be e.g. titanium or gold. The fluid-shielding cover cap 6 may be bonded to the surface 5 with a wafer-to-wafer technology or die-to-wafer technology or die-to-die technology e.g. using a soldering layer 11 as described with reference to FIG. 1.

FIG. 4 shows a schematic representation of a top view of the optical assembly 1 shown in FIG. 2 with a multi-loop antenna 15 placed at a peripheral area of the surface 5, i.e. having a circumference which is outside of the optical interaction area 4 and the cover cap 6. In this embodiment, the antenna 15 is positioned at a circumference of the substrate 2. This allows to maximise the surface area of the (possibly multi-loop) antenna 15 which enhances data and power exchange capabilities. The multi loop antenna 15 can be arranged on an upper side (see embodiment of FIG. 2) or on a bottom side of the substrate 2 (see embodiment of FIG. 3). The antenna 15 may be used for transferring collected sensor data externally and/or to transfer power. The antenna 15 may be provided using a suitable method, e.g. depositing conducting layer(s) onto the substrate 2.

FIG. 5 shows a cross sectional view of an even further embodiment of the present invention optical assembly 1. In this embodiment, the optical assembly 1 is an active implantable medical device (AIMD), which is an active device which may be introduced in the body of living creatures, such as a plant or an animal or a human being. In such an application, the AIMD is arranged to have a direct contact with body fluids such as blood, interstitial fluid, saliva, aqueous humour, amniotic fluid, etc. In some embodiments, the optical assembly 1 is arranged as an optical sensor for sensing glucose, or alternatively/additionally for other substances, such as urea, lactate, creatinine, triglyceride, protein, cholesterol, ethanol, ketones and hormones. Implants used in a body of living creatures do not have any sharp edges or corners, because they can cause internal injury. In this further embodiment, the optical assembly 1 comprises a protection layer 25 around (i.e. surrounding) the optical assembly 1. Optionally an aperture for the optical interaction area 4 is provided. The protection layer 25 can have e.g. a micro structured surface or a smooth and rounded outer surface. The protection layer 25 for example can be a polymer layer which can be coated after the hermetic sealing of the optical assembly 1. The protection layer 25 can be designed and applied efficiently in such a way that the optical interaction area 4 is kept open to have a direct exposure to the sensing environment. Optionally, the optical interaction area 4 can be provided with a thin anti-corrosive top layer, with a predetermined thickness so as not to affect the sensing and being for example in one or more materials from the group of Silicon Carbide (SiC), Diamond Like Carbon (DLC), $TiO_2$, or $Al_2O_3$.

It is an advantage of this embodiment that it allows miniaturisation of the optical assembly 1. The miniaturization enables the optical assembly 1 to be as compact that the natural flow of bodily fluids or the natural diffusion of a substance, e.g. present in living creatures enables the possibility for sensing and for continuous monitoring of the substance. The sensing can be performed e.g. using optical characterization techniques which do not require reagents or other auxiliary substances. These advantages result in a reliable and long term usable optical assembly 1 without the need for significant interference of users.

In an alternative or additional embodiment, the optical microsystem assembly 1 further comprises an energy supply device 16 positioned within the hermetically sealed cavity 9. An energy supply device is used for supplying the required energy for all (opto-)electronic components 8, 16, 17 of the optical assembly 1 as discussed with reference to the various embodiments described above. The energy supply device 16 is in one specific embodiment an energy storage, e.g. a micro battery, or in a further specific embodiment an energy harvesting device. A micro battery supplies fixed energy density in a limited lifetime, depending on the size of micro battery and the energy demands of the (opto-)electronic components 8, 16, 17. In the further specific embodiment, the respective power demanding components 8, 16, 17 of the optical assembly 1 use an energy harvesting device which have longer lifetime and which can provide more comfort and safety compared to conventional devices. Energy harvesting devices generate electric energy from their surroundings through direct energy conversion; e.g. infrared radiant energy, thermal energy (solar-thermal, geothermal gradients of temperature, combustion), kinetic energy (wind, gravity, vibration), wireless transfer energy and RF radiation energy (inductive and capacitive coupling, e.g. using the antenna 15 described above with reference to the embodiments shown in FIGS. 2, 3 and 4). In the present invention embodiments, the optical feedthrough 10 may alternatively or additionally be used for providing optical energy from the outside to optoelectronic components inside the sealed cavity 9. The energy harvesting from human or environmental sources provide an effective alternative in case of implanted assemblies 1, e.g. using kinetic energy from body motion.

It is noted that in the embodiments described above with reference to FIG. 1-5, the active component 8 may be a radiation source whose radiation is used for e.g. sensing a substance.

The light source might be one or more broadband sources (LED, SLED), a single narrow-band source (e.g. a laser, such as a VCSEL, a DFB laser, a DBR laser), or an ensemble of narrow-band sources. The reference made to light or radiation in the present description refers to electromagnetic radiation. The light envisaged is radiation having a suitable wavelength or wavelength range for sensing a certain substance. In some embodiments light used will be infrared radiation, e.g. visible light radiation, near IR radiation or mid IR radiation. The fabrication and integration technologies for the silicon photonics are well developed in the telecommunication wavelengths (1310 nm, 1550 nm) which could be exploited for extending to the wavelength range of interest with easy, reliable and cost-effective manufacturing of the present invention optical assembly 1.

Additionally photodetectors may be integrated on the surface 5 within the sealed cavity 9 provided by the hermetically sealed cover cap 6. The photodetectors are used to convert the optical signals into electrical signals. The photodetector might be a photodiode or a photoconductor, or an ensemble of these elements. There may be additional electronic components 16, 17 integrated within the hermetic sealing such as a monitor photodiode, a wireless module or even an amplifier.

The often bulky electronic and optoelectronic components 8, 16, 17 as described above are integrated to the substrate 2 and electrically connected to the metal bond pads on the surface 5. The integration of the components 8, 16, 17 can be for example monolithically, heterogeneously or by a hybrid method. Monolithic integration is the integration technology that uses a single processing flow to process the diverse components potentially using different materials, e.g. integrated germanium detectors in silicon photonics IC. Heterogeneous integration is the integration technology for which the components are processed in separate process flows, which are then integrated at die or wafer level, e.g. BCB bonding, wafer bonding, and other bonding schemes, 3D integration. Hybrid integration is the integration of components or materials on processed photonic integrated platforms, e.g. flip-chipping of detectors, bumping, gluing, wire bonding, co-packaging, etc.

The present invention in a further aspect relates to a method for manufacturing an optical assembly, e.g. an optical assembly 1 according to any one of the embodiments described herein. The method comprises providing a substrate 2 with an integrated optical microstructure 3 forming an optical interaction area 4, and providing at least one active component 8 on a surface 5 adjacent to the optical interaction area 4. The method further comprises providing a cover cap 6 on a part of the substrate 2 to form a sealed cavity 9 where at least one active component 8 is positioned. As discussed above the method of manufacturing the optical assembly 1 may further comprise providing at least one optical feedthrough 10 extending from the sealed cavity 9 to the exposed optical interaction area 4. In a further embodiment, the method of manufacturing the optical microsystem assembly 1 further comprises providing at least one electrical feedthrough 20 extending from inside the sealed cavity 9 to an area outside of the sealed cavity 9 in substrate 2. As discussed above referring to the embodiment shown in FIG. 5, the method of manufacturing the optical microsystem assembly 1 may further comprise providing a protection layer 25 around the optical assembly 1, possibly with an aperture for the optical interaction area 4.

Hermetic sealing of the optical assembly 1 embodiments as described herein may be performed at a die or at a wafer level. Die level sealing requires individual process for each die and optical assembly 1, which increases packaging cost and labour time and decreases the process yield and reliability. On the other hand, wafer level hermetic sealing provides a better solution in all the above aspects by using well-known techniques, such as thin film encapsulation or wafer-to-wafer bonding, providing low-cost packaging solutions. Hermetic sealing by wafer-to-wafer bonding employs a separate cap wafer for the sealing purposes, which provides perfect mechanical robustness for the protection of the sensors. In an alternative or additional embodiment, the method of manufacturing the optical microsystem assembly 1 further comprises sealing the cover cap 6 to the substrate 2 by a wafer-level packaging technology (WLP).

The present invention has been described above with reference to a number of exemplary embodiments as shown in the drawings. Modifications and alternative implementations of some parts or elements are possible, and are included in the scope of protection as defined in the appended claims.

The invention claimed is:

1. An implantable optical sensor comprising a photonic integrated circuit comprising a substrate, an optical microstructure integrated with the substrate, and at least one active component that comprises a light source,
    wherein the optical microstructure is locally etched open to form an optical interaction area on a part of a surface of the substrate to expose light from the light source,
    wherein the photonic integrated circuit further comprises a cover cap on a part of the substrate adjacent to the optical interaction area, the cover cap being hermetically sealed to the substrate at a wafer level or at a die level, and the light source is positioned in a sealed cavity formed between the surface of the substrate and the cover cap,
    wherein the substrate comprises at least one optical feedthrough extending from the sealed cavity to the optical interaction area, the optical feedthrough being an embedded waveguide in the substrate, and
    wherein the optical microstructure is an integrated waveguide connected to the optical feedthrough and is configured to confine the light from the light source within the sealed cavity and expose the light at the optical interaction area.

2. The implantable optical sensor according to claim 1, further comprising at least one electrical feedthrough extending from the sealed cavity to an area of the substrate outside of the sealed cavity.

3. The implantable optical sensor according to claim 2, wherein the at least one electrical feedthrough extends from the sealed cavity to a surface of the substrate opposite to the cover cap.

4. The implantable optical sensor according to claim 1, wherein the cover cap is made of a fluid-sealing material selected from: glass, metal, silicon, polymer, or a combination thereof.

5. The implantable optical sensor according to claim 1, wherein the cover cap comprises an electromagnetic shielding layer.

6. The implantable optical sensor according to claim 1, further comprising a protection layer around the implantable optical sensor to prevent internal injury.

7. The implantable optical sensor according to claim 6, wherein the protection layer has an aperture for the optical interaction area.

8. The implantable optical sensor according to claim 1, further comprising an energy supply device positioned in the sealed cavity.

9. The implantable optical sensor according to claim 1, wherein the at least one active component is attached to the surface of the substrate within the sealed cavity.

10. The implantable optical sensor according to claim 1, further comprising an antenna.

11. The implantable optical sensor according to claim 1, wherein the optical interaction area is a sensing area.

12. The implantable optical sensor according to claim 1, wherein a bottom edge of the cover cap, with which the cover cap is hermetically sealed to the substrate, is flangeless and is in direct contact with the surface of the substrate.

13. The implantable optical sensor according to claim 1, wherein the optical feedthrough is arranged to provide bidirectional optical communication between the inside of the sealed cavity and the optical interaction area.

14. A method of manufacturing an implantable optical sensor, the method comprising:
    providing a photonic integrated circuit comprising a substrate with an integrated optical microstructure, at least one active component that comprises a light source, and at least one optical feedthrough extending from an optical interaction area to a part of the substrate adjacent to the optical interaction area, wherein the optical feedthrough is an embedded waveguide in the substrate;

locally etching the optical microstructure open to form the optical interaction area on a part of the surface of the substrate to expose light from the light source;

providing the light source on the surface of the substrate on the part adjacent to the optical interaction area;

providing a cover cap on said part of the substrate to form a sealed cavity where the at least one active component is positioned; and sealing the cover cap to the substrate, the cover cap being hermetically sealed to the substrate by wafer-level or die-level hermetic packaging technique, wherein the optical microstructure is an integrated waveguide connected to the optical feedthrough and is configured to confine the light from the light source within the sealed cavity and expose the light at the optical interaction area.

15. The method according to claim 14, further comprising providing at least one electrical feedthrough extending from the sealed cavity to an area of the substrate outside of the sealed cavity.

16. The method according to claim 14, further comprising providing a protection layer around the implantable optical sensor and leaving an aperture for the optical interaction area.

17. The method according to claim 14, wherein the cover cap is hermetically sealed to the substrate by laser bonding or anodic bonding.

18. The method according to claim 14, wherein a bottom edge of the cover cap, with which the cover cap is hermetically sealed to the substrate, is flangeless and wherein prior to said sealing said bottom edge is brought in direct contact with the surface of the substrate.

* * * * *